US00PP23817P2

(12) United States Plant Patent
Hartman

(10) Patent No.: US PP23,817 P2
(45) Date of Patent: Aug. 6, 2013

(54) ***CALADIUM* PLANT NAMED 'BOMBSHELL'**

(50) Latin Name: *Caladium×hortulanum*
Varietal Denomination: Bombshell

(76) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 13/374,456

(22) Filed: Dec. 29, 2011

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Kent L Bell
(74) *Attorney, Agent, or Firm* — C. A. Whealy

(57) ABSTRACT

A new and distinct cultivar of *Caladium* plant named 'Bombshell', characterized by its upright plant habit; intermediate to tall plant size; uniform plant habit; vigorous and dense growth habit; fancy-type leaves with dark red to greyed purple-colored venation and interveinal areas surrounded with dark green-colored borders; and good landscape performance.

4 Drawing Sheets

Botanical designation: *Caladium×hortulanum.*
Cultivar denomination: 'BOMBSHELL'.

CROSS-REFERENCED TO CLOSELY-RELATED APPLICATIONS

Title: *Caladium* Plant Named 'Party Punch'
Applicant: Robert Dale Hartman
Filed: Dec. 29, 2011
Ser. No. 13/374,460

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Bombshell'.

The objective of the Inventor's breeding program is to create new *Caladium* plants that have uniform plant habit, exceptional container and garden performance and attractive foliage coloration.

The new *Caladium* plant originated from a cross-pollination made by the Inventor on Apr. 15, 2007, in Avon Park, Fla. of a proprietary selection of *Caladium×hortulanum* identified as code number WS-03-36, not patented, as the female, or seed, parent with *Caladium×hortulanum* 'Red Flash', not patented, as the male, or pollen, parent. The new *Caladium* plant was discovered and selected by the Inventor as a single plant within the progeny of the stated cross-pollination in a controlled outdoor nursery environment in Zolfo Springs, Fla. on Sep. 15, 2008.

Asexual reproduction of the new *Caladium* plant by 'chipping' the tubers (cutting the tuber into segments each segment containing an axillary bud and tuber cortical tissue) in a controlled outdoor nursery environment in Lake Placid, Fla. since Apr. 14, 2009 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices.

The phenotype may vary somewhat with variations in environmental conditions such as temperature and light intensity, without, however, any variance in genotype.

The following traits have been repeatedly observed and are determined to be the unique characteristics of 'Bombshell'. These characteristics in combination distinguish 'Bombshell' as a new and distinct *Caladium* plant:

1. Upright plant habit; intermediate to tall plant size.
2. Uniform plant habit.
3. Vigorous and dense growth habit.
4. Fancy-type leaves with dark red to greyed purple-colored venation and interveinal areas surrounded with dark green-colored borders.
5. Good landscape performance and tolerant to full sun conditions.

Plants of the new *Caladium* differ primarily from plants of the female parent selection in the following characteristics:

1. Plants of the new *Caladium* are taller and more upright than plants of the female parent selection.
2. Leaves of plants of the new *Caladium* are ovate in shape whereas leaves of plants of the female plant selection are lanceolate in shape.
3. Plants of the new *Caladium* and the female parent selection differ in leaf coloration as leaves of plants of the female parent selection have grey green-colored venation and interveinal areas and dark green-colored borders.

Plants of the new *Caladium* differ primarily from plants of the male parent, 'Red Flash', in the following characteristics:

1. Plants of the new *Caladium* grow faster than plants of 'Red Flash'.
2. Plants of the new *Caladium* and 'Red Flash' differ in leaf coloration as leaves of plants of 'Red Flash' have red-colored venation and interveinal areas with pink and white-colored spots and dark green-colored borders.

Plants of the new *Caladium* can be compared to plants of *Caladium* 'Party Punch', disclosed in a U.S. Plant patent application Ser. No. 13/374,460. Plants of the new *Caladium* are more upright than plants of 'Party Punch'. In addition, plants of the new *Caladium* and 'Party Punch' differ in leaf petiole and leaf coloration.

Plants of the new *Caladium* can be compared to plants of *Caladium* 'Rosebud', not patented. In side-by-side comparisons conducted in Avon Park, Fla., plants of the new *Caladium* differed primarily from plants of 'Rosebud' in the following characteristics:

1. Plants of the new *Caladium* were taller and more vigorous than plants of 'Rosebud'.
2. Plants of the new *Caladium* grew slower than plants of 'Rosebud'.
3. Leaves of plants of the new *Caladium* were more elongate than and not as round as leaves of plants of 'Rosebud'.
4. Plants of the new *Caladium* and 'Rosebud' differed in leaf coloration as leaves of plants of 'Rosebud' had pink-colored venation and interveinal areas surrounded by whitish-colored areas and green-colored borders.

Plants of the new *Caladium* can also be compared to plants of *Caladium* 'Carolyn Whorton', not patented. In side-by-side comparisons conducted in Avon Park, Fla., plants of the new *Caladium* differed primarily from plants of 'Carolyn Whorton' in the following characteristics:

1. Plants of the new *Caladium* were taller than plants of 'Carolyn Whorton'.
2. Leaves of plants of the new *Caladium* were flatter than leaves of plants of 'Carolyn Whorton'.
3. Plants of the new *Caladium* and 'Carolyn Whorton' differed in leaf coloration as leaves of plants of 'Carolyn Whorton' had deep rose red-colored venation with pink-colored blotches and green-colored borders.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Bombshell' grown in a 15-cm container in a shadehouse.

The photograph at the top of the second sheet is a side perspective view of typical plants of 'Bombshell' grown in an outdoor nursery.

The photograph at the bottom of the second sheet is a close-up view of typical freshly-harvested tubers and roots of 'Bombshell'.

The photograph at the top of the third sheet is a comparison view of typical plants of 'Bombshell' grown in 15-cm containers, the plant on the left has not had its tuber de-eyed and the plant on the right has had its tuber de-eyed prior to planting.

The photograph at the bottom of the third sheet is a close-up view of a typical inflorescence of 'Bombshell'.

The photograph at the top of the fourth sheet is a comparison view of typical potted plants of the female parent selection (left), 'Bombshell' (center) and the male parent, 'Red Flash' (right).

The photograph at the bottom of the fourth sheet is a comparison view of typical potted plants of 'Rosebud' (left), 'Bombshell' (center) and 'Carolyn Whorton' (right).

DETAILED BOTANICAL DESCRIPTION

The aforementioned photographs and following observations and measurements describe plants grown during the spring in 15-cm containers in Avon Park, Fla. in a polypropylene-covered shadehouse (30% shade) and plants grown during the autumn in ground beds in an outdoor nursery in Zolfo Springs, Fla. All plants were grown under environmental conditions and cultural practices which approximate those generally used in commercial shadehouse and outdoor nursery *Caladium* production. During the production of the plants, day temperatures ranged from about 29° C. to 33° C. (shadehouse) or 29° C. to 35° C. (outdoor nursery), night temperatures ranged from about 22° C. to 25° C. (shadehouse) or 23° C. to 26° C. (outdoor nursery) and light levels were about 8,000 foot-candles (shadehouse) or 10,000 to 12,000 foot-candles (outdoor nursery). Plants grown in the shadehouse were eight weeks old when the photographs and the detailed description were taken. Plants grown in the outdoor nursery were seven months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Bombshell'.

Parentage:

*Female, or seed, parent.*—Proprietary selection of *Caladium×hortulanum* identified as code number WS-03-36, not patented.

*Male, or pollen, parent.*—*Caladium×hortulanum* 'Red Flash', not patented.

Propagation:

*Type.*—By "chipping" the tubers.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate to elliptic in shape. Height: About 3.5 cm. Diameter: About 5.6 cm. Texture: Thick and starchy; somewhat brittle. Color: Epidermis, freshly harvested, close to 199A to 199B and 200A, faintly tinged with close to 181C to 181D; epidermis, dried tuber, close to 200A to 200B; cortical tissue, close to 4C to 4D; axillary buds, close to 37C to 37D. Root description: Thick, fleshy contractile roots; color, close to 155C. Rooting habit: Few lateral branches; moderately dense.

Plant description:

*Plant type.*—Herbaceous perennial; suitable as a potted plant in containers 15-cm to 25-cm and suitable as a landscape plant in shaded and full sunlight areas.

*Plant and growth habit.*—Upright plant habit; intermediate to tall plant size; inverted triangle; vigorous and dense growth habit; rapid growth rate; leaf petioles and leaves arise from one or more growing points on tubers; petioles mostly upright and arching outwardly with development.

*Plant height, from soil level to top of foliar plane, shadehouse-grown potted plants.*—About 30 cm to 38 cm.

*Plant height, from soil level to top of inflorescences, shadehouse-grown potted plants.*—About 20 cm.

*Plant diameter or spread, shadehouse-grown potted plants.*—About 29 cm to 37 cm.

*Number of clumps per plant, shadehouse-grown potted plants.*—About two to three from de-eyed tubers.

*Cataphylls, shadehouse-grown potted plants*.—Length: About 7 cm. Width: About 9 mm. Shape: Ligulate. Apex: Emarginate to acuminate. Base: Sheathing the stem. Color, outer surface: Close to N170D stippled and tessellated with close to 147B tinged with close to 200B; with development, color becoming closer to 200B. Color, inner surface: Close to N155C, outer surface colors and patterns visible.

Foliage description:

*Length, shadehouse-grown potted plants*.—About 16 cm to 22 cm.

*Width, shadehouse-grown potted plants*.—About 11.3 cm to 15.9 cm.

*Shape*.—Ovate.

*Apex*.—Acuminate.

*Base*.—Sagittate, peltate.

*Margin*.—Entire; mostly flat with a few broad undulations.

*Texture, upper surface*.—Smooth, glabrous.

*Texture, lower surface*.—Smooth, glabrous; glaucous.

*Venation pattern*.—Pinnate.

*Color, shadehouse-grown potted plants*.—Developing leaves, upper surface: Basal notch: Close to 187A. Venation between basal notch and petiole attachment: Close to 187A. Midrib and primary venation: Between 187A and 53A. Areas surrounding the primary venation: Close to 184A and 185A. Interveinal areas: Random sectors and spots, close to 183A, 185A, 147A and 155A. Borders: Close to 147A; random flecks, close to N186A. Margins: Close to 187B. Developing leaves, lower surface: Basal notch: Close to 187B. Venation between basal notch and petiole attachment: Close to 187B. Midrib and primary venation: Close to 191A tinged and streaked with close to 182B and 182C. Areas surrounding the primary venation: Close to 183B. Interveinal areas: Random sectors and spots, close to 145D, 150D, 182D and 49D. Borders: Close to 191A and 189A. Margins: Close to 187B. Fully expanded leaves, upper surface: Basal notch: Close to N186C. Venation between basal notch and petiole attachment: Close to N186C. Midrib and primary venation: Close to N186C. Areas surrounding the primary venation: Close to 53B and 185A. Interveinal areas: Close to 182C to 182D, 183A and 187A. Borders: Darker than between N189A and 147A. Margins: Close to 187B. Fully expanded leaves, lower surface: Basal notch: Close to N187C. Venation between basal notch and petiole attachment: Close to N187C. Midrib: Close to 191A streaked with close to 181A and 182A. Primary venation: Close to 191A tinged with close to 189A. Areas surrounding the primary venation: Close to 183C to 183D. Interveinal areas: Random sectors and spots, close to 182D. Borders: Darker than between 189A and 191A. Margins: Close to 187B.

*Petiole*.—Aspect: Mostly erect, slightly outwardly arching with development; flexible. Length, shadehouse-grown potted plants: About 22 cm to 26 cm. Diameter, distal, shadehouse-grown potted plants: About 3.5 mm to 5 mm. Diameter, proximal, shadehouse-grown potted plants: About 5 mm to 9 mm. Color, shadehouse-grown potted plants: Close to N170D or N170D tinged with close to 182D, stippled and tessellated with close to 200C, variably tinged with close to 147B and variably striped with close to 200B to 200C. Wing length, shadehouse-grown potted plants: About 3 cm to 5.9 cm. Wing diameter, shadehouse-grown potted plants: About 4 mm to 8 mm. Wing color, shadehouse-grown potted plants, outer surface: Close to N170D stippled and tessellated with close to 147B and tinged with close to 200B. Wing color, shadehouse-grown potted plants, inner surface: Close to N155C, outer surface colors and patterns visible.

Inflorescence description: Inflorescences observed on eight-week old shadehouse-grown potted plants.

*Inflorescence arrangement*.—Upright hooded spathes surrounding a columnar spadix borne on a tall upright scape; spadix with sessile, simple female and male flowers separated into two zones; female flowers arranged on the lower one-third of the spadix; male flowers arranged on the upper two-thirds of the spadix; sterile flowers develop at junction of female and male flower zones; near this junction, the spathe constricts and surrounds and encloses the female flowers; spathe open and cupped around male flowers.

*Fragrance*.—Night fragrant; moderate jasmine-like fragrance with camphor-like note.

*Natural flowering season/longevity*: Plants of the new *Caladium* typically flower during the spring or early summer in central Florida; flowers develop about eight weeks after growth commences; inflorescences last about three days before fading; inflorescences persistent.

*Spathe*.—Length: About 6.9 cm; open length, about 4.2 cm and closed length, about 2.7 cm. Width, distal: About 3 cm. Width, proximal: About 2 cm. Width, at constriction: About 1.2 cm. Shape: Ovate to elliptic. Apex: Acuminate. Base: Tapering to the peduncle. Margin: Entire; slightly reflexed. Texture, front surface: Smooth, glabrous. Texture, rear surface: Smooth, glabrous; glaucous. Color, front surface: Upper two-thirds: Close to 155C and 192D; with development, color becoming closer to 199B. Lower one-third: Close to 148C; towards the base, close to N77A and 187A; color does not change with development Color, rear surface: Upper two-thirds: Close to 155C tinged with close to 145C and 146D. Lower one-third: Close to 147B, 147C and 146A variably streaked and flushed with close to 187B and 187C.

*Spadix*.—Length: About 6.2 cm. Length, male flower zone: About 3.4 cm. Length, sterile zone: About 1.3 cm. Length, female flower zone: About 1.5 cm. Diameter, male flower zone: About 8 mm. Diameter, sterile flower zone: About 6.5 mm. Diameter, female flower zone: About 8 mm. Shape: Columnar. Apex: Obtuse. Base: Obtuse. Aspect: Upright. Color, mature, male zone: Close to 158B to 158C. Color, mature, sterile zone: Close to 158B to 158C. Color, mature, female zone: Close to 18B. Male flowers: Quantity per spadix: About 110. Shape: Obovate. Height: About 3 mm. Diameter: About 3 mm. Pollen amount: Moderate. Pollen color: Close to 11C. Female flowers: Quantity per spadix: About 85. Shape: Ovate. Height: About 3 mm. Diameter: About 2 mm. Stigma color: Close to 18B. Ovary color: Close to 155C.

*Scape*.—Length: About 13.1 cm. Diameter: About 4.5 mm. Strength: Sturdy; flexible. Aspect: Erect or slightly curved. Texture: Smooth, glabrous; glaucous. Color: Close to 199A tinged with close to 147B and streaked with close to N199B.

*Seeds and fruits*.—Seed and fruit development have not been observed on plants of the new *Caladium*.

Disease & pest tolerance/resistance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Bombshell' as illustrated and described.

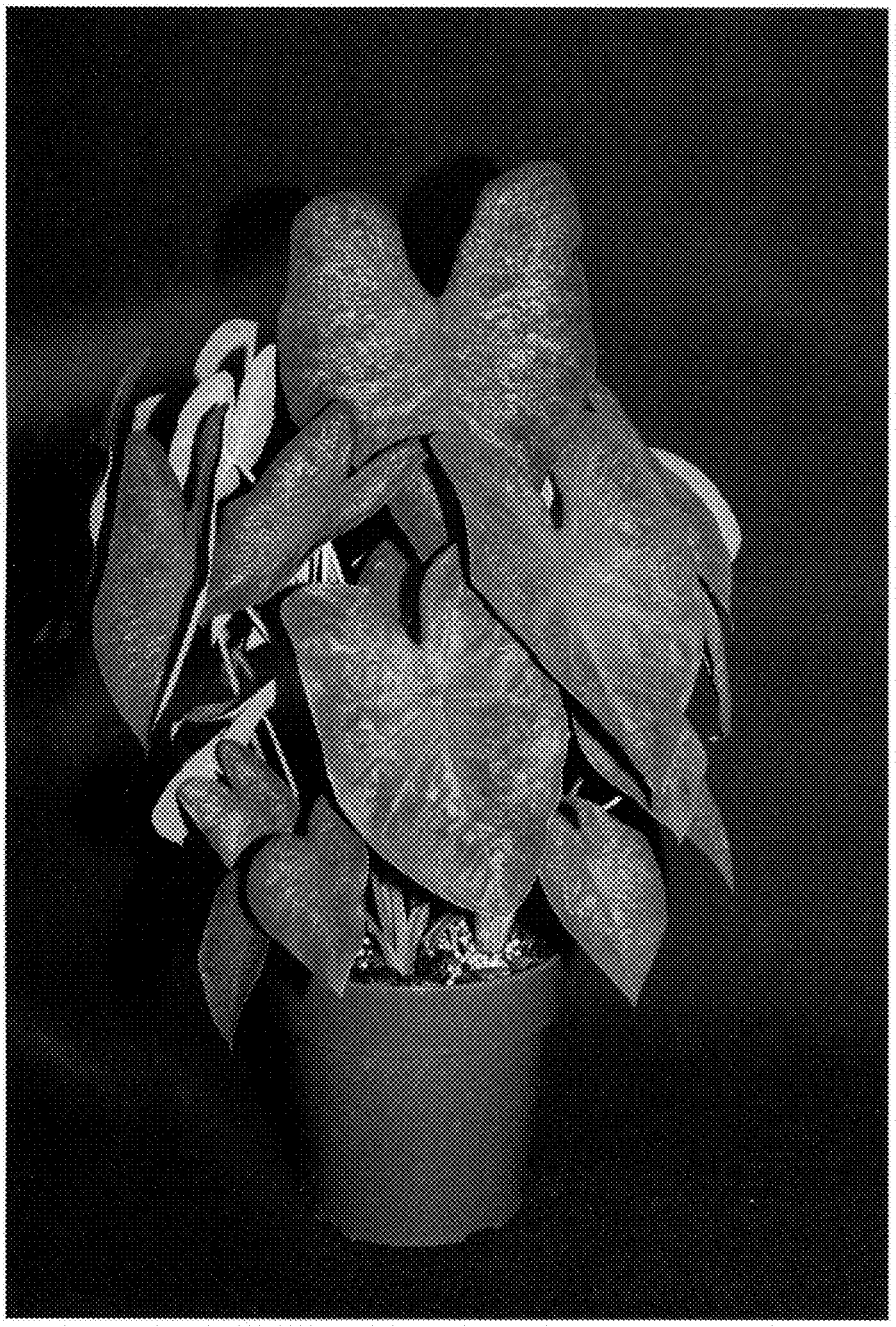

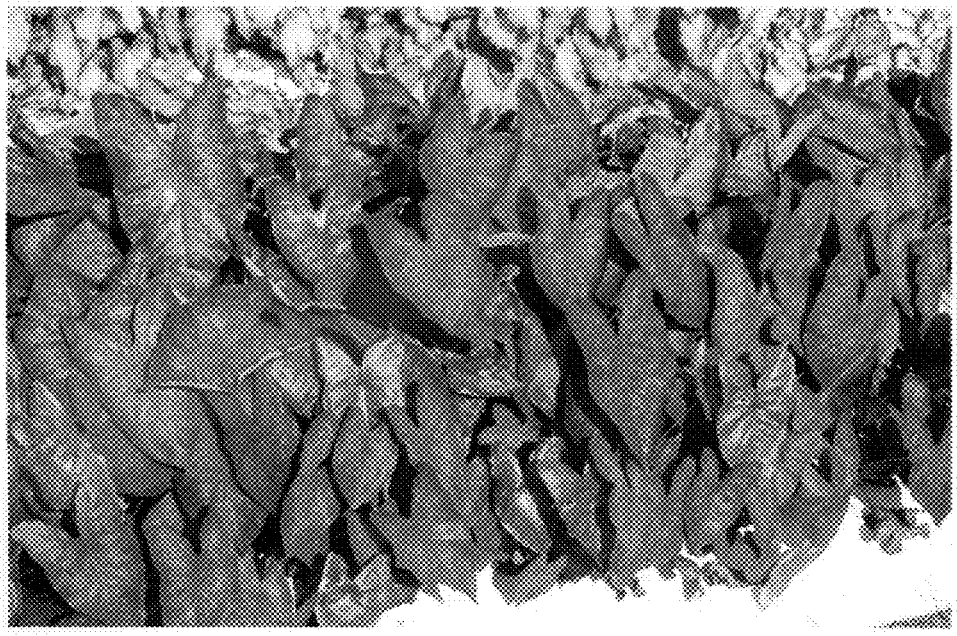
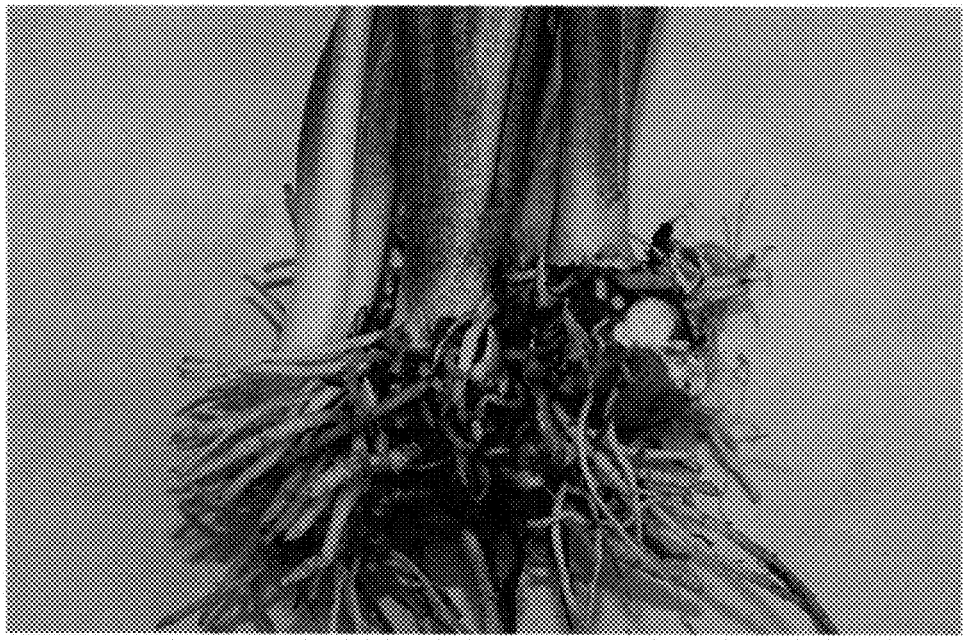

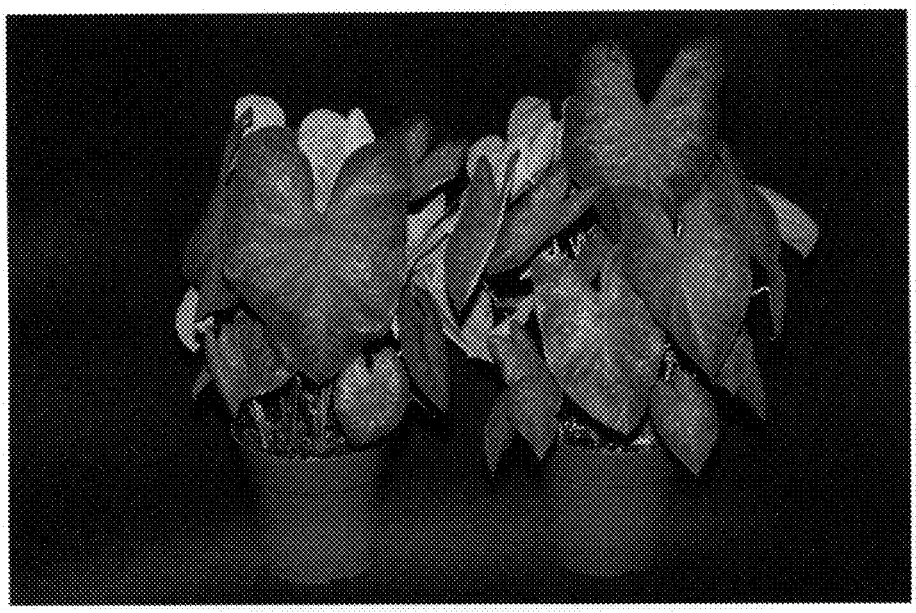
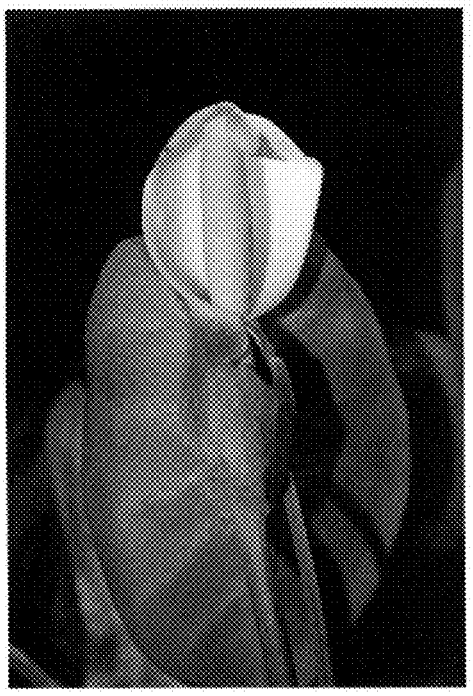

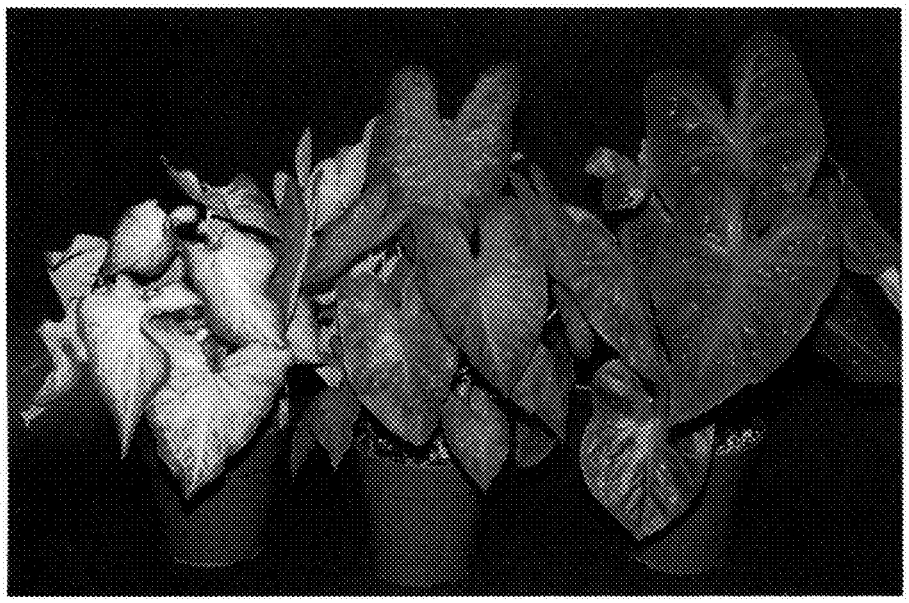
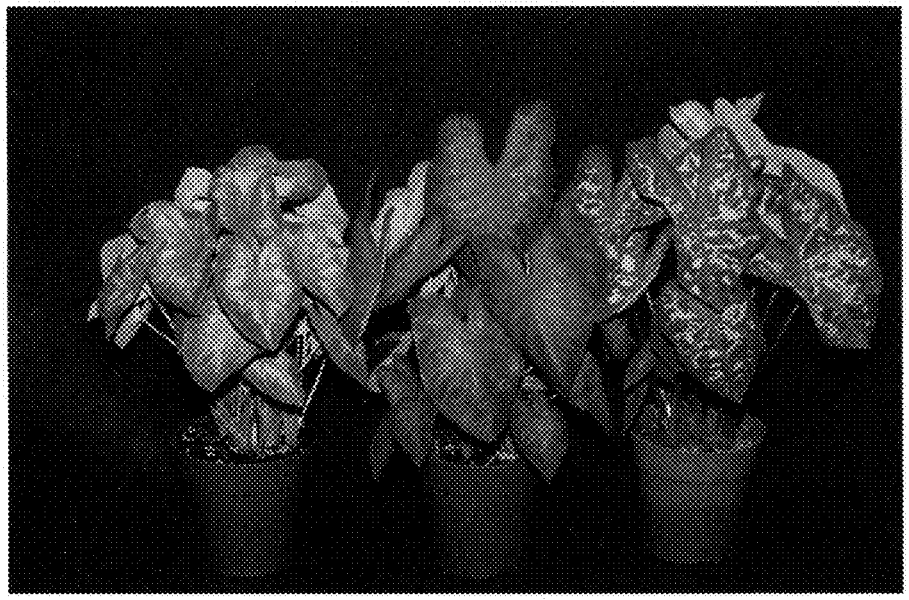

* * * * *